United States Patent [19]

Teichmüller et al.

[11] Patent Number: 4,474,701

[45] Date of Patent: Oct. 2, 1984

[54] PROCESS FOR THE SEPARATION OF 4-ANDROSTEN-3,17-DIONE AND 1,4-ANDROSTADIEN-3,17-DIONE

[75] Inventors: Gerhard Teichmüller, Jena; Joachim Rabe, Orlamuende; Harry Henkel, Apolda, all of German Democratic Rep.

[73] Assignee: Veb Jenapharm Jena, Jena, German Democratic Rep.

[21] Appl. No.: 474,314

[22] Filed: Mar. 10, 1983

[51] Int. Cl.$^3$ .................................................. C07J 1/00
[52] U.S. Cl. ................................. 260/397.3; 260/397.4
[58] Field of Search .......................... 260/397.3, 397.4

[56] References Cited

U.S. PATENT DOCUMENTS 4,144,254  3/1979  Imai et al. ......................... 260/397.3

Primary Examiner—Elbert L. Roberts

Attorney, Agent, or Firm—Michael J. Striker

[57] ABSTRACT

A process is disclosed for the separation of 4-androsten-3,17-dione/1,4-androstadien-3,17-dione mixtures, which are produced, e.g., upon microbiological sterol-side chain decomposition, through conversion of said mixture into a mixture of 17$\beta$-cyano-17$\alpha$-hydroxy-4-androsten-3-one/17$\beta$-cyano-17$\alpha$-hydroxy-1,4-androstadien-3-one, from which the difficultly soluble 17$\beta$-cyano-17$\alpha$-hydroxy-4-androsten-3-one is separated in crystalline form through filtration, and the 17$\beta$-cyano-17$\alpha$-hydroxy-1,4-androstadiene remaining in the mother liquor is re-split, directly or after extraction with organic solvent, by treatment in alkaline medium, into 1,4-androstadien-3,17-dione, and isolated as such. The separation of the products follows in high yields, and in sufficient purity for further working-up in the synthesis of androstane and pregnane derivatives, as well as estratrienes.

6 Claims, No Drawings

PROCESS FOR THE SEPARATION OF 4-ANDROSTEN-3,17-DIONE AND 1,4-ANDROSTADIEN-3,17-DIONE

BACKGROUND OF THE INVENTION

The present invention concerns a new process for the separation of mixtures of 4-androsten-3,17-dione and 1,4-androstadien-3,17-dione, resulting upon microbiological sterol-side chain decomposition.

4-androsten-3,17-dione and 1,4-androstadien-3,17-dione are important starting materials for the synthesis of androstan- and pregnan-derivatives, as well as estratrienes.

With the technical use of microbiological sterol side-chain decomposition, 4-androsten-3,17-dione and 1,4-androstadien-3,17-dione are easily accessible products for the synthesis of steroids.

4-androsten-3,17-dione is the starting material for the synthesis of androstan derivatives such as testosterone, methyltestosterone, spironolactone, among others, pregnan derivatives such as progesterone, 17α-hydroxyprogesterone, hydrocortisone, among others.

1,4-androstadien-3,17-dione is easily converted into estratriene derivatives by aromatization reactions. The 1,4-androstadien-3,17-dione accessible in this manner is more economically favorable for the synthesis of estratrienes than the production of these products through total synthesis.

According to processes described in the literature, involving microbiological sterol-side chain decomposition, as a rule mixtures of 4-androsten-3,17-dione and 1,4-androstadien-3,17-dione of different composition, in addition to small amounts of other decomposition products, are obtained (AP No. 130 789 Upjohn, DE-AS No. 2 703 645 Upjohn). The yields amount to an average 50% up to 80% of the 4-androsten-3,17-dione/1,4-androstadien-3,17-dione mixture.

Through the use of different organisms for the sterol-side chain decomposition, the microbiological decomposition processes can be so controlled that not only 4-androsten-3,17-dione but also 1,4-androstadien-3,17-dione are produced as main products, and the other mixture components are produced in order of magnitude of about 5 up to 25%.

For the separation of such a mixture, different processes are described in the literature. Thus, the separation and purification of 1,4-androstadien-3,17-dione from the steroid mixture of 1,4-androstadien-3,17-dione and cholesterin, isolated by microbiological sterol-side chain decomposition, follow through treatment with A-coal and subsequent column chromatography (JA No. 7 514 958, Tayoko Co., Ltd.).

According to another process (JA No. 78 127 454, Mitsubishi), the 3-keto-1,4-diene-steroid is converted through treatment with K-t-butylate into the corresponding 3-keto-1,5-diene-derivative, and subsequent hydrogenation with a Rh/c-catalyst in a heterogeneous system into 5-androsten-3,17-dione. The yields in this two-stage process amount to about 50–60%.

A further process (JA No. 78 130 650, Mitsubishi) provides for the direct hydrogenation of 3-keto-1,4-diene-steroid with rhodium-tris-(triphenylphosphine)-chloride-catalysts in homogeneous systems. The yield of 3-keto-4-an-steroids amounts to about 90%, relative to the 3-keto-4en-steroid contained in the mixture.

The separation of the steroid from this steroid-catalyst mixture requires great expenditures, which are connected with further losses of substance, the total yield lowering to about 80% of the obtained decomposition product (JA No. 78 127 452, Mitsubishi; No. 78 130 649, Mitsubishi). A further disadvantage of these methods is that the selectivity of the catalysts in these reactions is not sufficient, and up to 5% completely hydrogenated 5α-androstan-3,17-dione are obtained in the reaction mixture (JA No. 78 127 452, Mitsubishi). It has also already been suggested to selectively reduce the 1,4-androstadiene-3,17-dione present in the mixture into 4-androsten-3,17-dione, through use of a second microbiological stage (WP No. 137 361).

All of the previously suggested processes require, however, high additional expenditures, which are connected moreover with further decreases in yield.

Since both products, 1,4-androstadien-3,17-dione, particularly though 4-androsten-3,17-dione, are required for steroid synthesis, according to the methods previously described in the literature, different processes for the production of these products are necessary, whereby the separation of the second, androstan derivative, contained in the produced mixture, for technical use is solved completely unsatisfactorily.

SUMMARY OF THE INVENTION

It is therefore an object of the present invention to develop a new process according to which the steroid mixture of 4-androsten-3,17-dione and 1,4-androstadien-3,17-dione, produced through microbiological sterol-side chain decomposition, is separated, through simple operations, without substantial loss in yield and in higher purity, which products can find use for further working-up in the synthesis of pregnane-, androstane- and estratriene-derivatives.

In surprising manner, it has been discovered that 4-androsten-3,17-dione and 1,4-androstadien-3,17-dione in mixture in solution, through reaction with cyanohydrines such as acetoncyanohydrine or other organic HCN-bound cyanide compounds, are converted into a mixture of 17β-cyano-17α-hydroxy-4-androsten-3-one and 17β-cyano-17α-hydroxy-1,4-androstadien-3-one, from which the difficultly soluble 17β-cyano-17α-hydroxy-4-androsten-3-one is separated by crystallization, and the 17β-cyano-17α-hydroxy-1,4-androstadien-3-one, remaining in the solution, is re-split and isolated, directly or after extraction with organic solvents according to known methods, into 1,4-androstadien-3,17-dione.

The known processes for the working-up of the product or product mixture obtained by microbiological sterin decomposition are oriented to:

converting the 1,4-androstadien-3,17-dione, contained in the 4-androsten-3,17-dione, through a microbiological reduction into 4-androsten-3,17-dione convert the 1,4-androstadien-3,17-dione, obtained as main product, through microbiological or chemical reduction into 4-androsten-3,17-dione.

The bases for these types of processes are, particularly, that the 4-androsten-3,17-dione which is the more important product for further working-up, and represents a substantial broadening in the provision of starting materials for the synthesis of androstanes and pregnanes, that 1,4-androstadien-3,17-dione is employed mainly for the synthesis of estratrienes, and the need for these products is by far smaller than the need for androstane and pregnane derivatives, and that according to the previous microbiological decomposition processes, predominantly 1,4-androstadien-3,17-dione or mixtures of 4-androsten-3,17-dione and 1,4-androstadien-3,17-dione were obtained.

The additional operations for converting 4-androsten-3,17-dione/1,4-androstadien-3,17-dione mixtures into a uniform product require additional technical apparatus, material expenditures as well as energy and labor.

Since both products, not only 4-androsten-3,17-dione but also 1,4-androstadien-3,17-dione respresent important starting materials for further steroid syntheses, one can with an advantageous separation process contribute to an optimal technical solution of the entire problem of provision of steroid starting materials.

The advantage of such a process design is also based upon the fact that for the production of both important starting materials (4-androsten-3,17-dione and 1,4-androstadien-3,17-dione) a microbiological decomposition process is still necessary, and with such a sterol-side chain decomposition process 4-androsten-3,17-dione and also 1,4-androstadien-3,17-dione are made available as starting materials.

Use of the process according to the present invention provides for converting the 4-androsten-3,17-dione and 1,4-androstadien-3,17-dione, resulting upon microbiological sterol side chain decomposition, into the corresponding cyanohydrines, and as such are separated by simple operations.

The production of cyanohydrine in the form of the 17β-cyano-17α-hydroxy derivative brings further economical advantages for the further working-up of these androstane derivatives, since particularly the 17β-cyano-17α-hydroxy-4-androsten-3-one represents an intermediate product, which also can be converted into compounds of the pregnane structure, according to simple chemical techniques. With the technical use of the separating method according to the present invention are provided likewise prerequisites for the simple technical utilization of the resulting products.

The working-up of these products for the synthesis of 17α-alkyltestosterone derivatives likewise requires no further operations for splitting of the cyanohydrine grouping, since through grignardization of the unprotected cyanohydrine grouping the direct alkylation in the 17α-position of the steroid molecule is possible.

For the working-up of the 17β-cyano-17α-hydroxy-1,4-androstadien-3-one into the aromatic C-18-steroids, the splitting of the cyanohydrine group is necessary, which can likewise be performed according to the present invention without substantial additional technical expenditures.

According to the present invention, the mixture of 4-androsten-3,17-dione and 1,4-androstadien-3,17-dione, resulting upon microbiological sterol side chain decomposition, is dissolved in a solvent or placed in suspension, and through addition of cyanohydrines such as e.g. acetoncyanohydrine or other HCN-bound cyanide compounds, in the presence of alkaline additives such as metal hydroxides, metal cyanides, metal carbonates or organic bases, in the pH-range from 7.5 up to 10.5, preferably from 8.3 up to 9.7, is reacted into the 17β-cyano-17α-hydroxy derivative mixture from 4-androsten-3,17-dione and 1,4-androstadien-3,17-dione, under equilibrium conditions at temperatures from 0° C. up to 60° C., preferably 30° C. up to 45° C.

The difficultly soluble 17β-cyano-17α-hydroxy-4-androsten-3-one crystallizes out from the reaction mixture, whereby through determined additives such as water or also organic solvents, the crystallization process is so controlled that from the 17β-cyano-17α-hydroxy-4-androsten-3-one present in the mixture, at least 96% up to 98% are recovered through crystallization, and the crystalline product contains less than 0.5 to 1% of 17β-cyano-17α-hydroxy-1,4-androstadien-3-one.

The control of the crystallization process requires a precise management through temperature regulation in connection with an aimed for addition of diluting agent in dependence upon the composition of the provided starting mixture. The separation of the crystallized reaction product follows through filtration, with yields of about 93 up to 96% of the theoretical amount, relative to the 4-androsten-3,17-dione portion contained in the mixture.

The 17β-cyano-17α-hydroxy-1,4-androstadien-3-one, remaining in the mother liquor, is converted into 1,4-androstadien-3,17-dione, through addition of alkali and light heating, and isolated as such or also after an extraction with organic solvents, subjected to the known re-splitting process is an alcohol solution, and isolated.

After a simple recrystallization from organic solvents such as alcohols, ketones, esters or aromatic hydrocarbons such as toluene, the 1,4-androstadien-3,17-dione contained in the mixture is already prepared, in a yield from about 75–80%, relative to the 1,4-androstadien-3,17-dione contained in the mixture, in sufficiently pure form for the further working-up.

The presentation of 17β-cyano-17α-hydroxy-androstane derivatives for separation of 4-androsten-3,17-dione and 1,4-androstadien-3,17-dione mixtures was surprising and not foreseeable, but in view of the economical utilization of the 4-androsten-3,17-dione/1,4-androstadien-3,17-dione, resulting upon microbiological sterol side chain decomposition, it is particularly valuable, since thereby in the total design of the process only one microbiological sterol-side chain decomposition process is necessary through separation of the resulting product mixture, the provision of 4-androsten-3,17-dione and 1,4-androstadien-3,17-dione for further working-up is realized without additional, expensive operations, the resulting products such as e.g. the 17β-cyano-17α-hydroxy-4-androsten-3-one already provides the first stage of the synthesis for the pregnane side-chain decomposition.

With the employment of this process for technical use, particularly the cyanohydrine synthesis again has particular significance for the synthesis of pregnane derivatives from androstane derivatives.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

EXAMPLE 1

5 g of 4-androsten-3,17-dione/1,4-androstadien-3,17-dione (3.75 g/1.25 g) are suspended in 21 ml methanol and reacted with 5 ml acetoncyanohydrine. The mixture is reacted with 2.1 ml water, adjusted to a temperature of 40° C. under stirring, and adjusted to a pH of 8.7 through addition of NaOH in methanol.

After about 40 minutes, the components are completely dissolved, and after a further 30 minutes crystallization of the formed 17β-cyano-17α-hydroxy-4-androsten-3-one takes place. The mixture is stirred a further 4 hours under the addition of 3 ml water, at 35°–40° C., and then allowed to stand overnight at room temperature. A temperature of 35° C. is then again adjusted, and under stirring, within 4 hours, a further 21 ml water is added. After the addition of water, it is cooled, within 2 hours, to 15° C., stirred yet 1 hour at this temperature, and then the crystallized product is sucked off. The crystallized product is washed in a frit with a little water, then extensively sucked dry, and dried in air.

Yield: 3.95 g (96% of theoretical amount, relative to the 4-androsten-3,17-dione contained in the mixture)

To the obtained mother liquor is added 50 ml water, then extracted several times with chloroform, the chloroform extract is then washed with water, and the product is compressed to dryness.

Dry residue: 1.45 g

The dry residue is withdrawn in 10 ml ethanol, reacted with 1 ml pyridine, and heated to reflux for 20 minutes. The solution is placed in water, extracted several times with chloroform, the chloroform solution is washed with water, and then compressed to dryness. The obtained residue is recrystallized from aqueous acetone.

Yield: 970 mg (77% of theoretical amount, relative to the 1,4-androstadiene-3,17-dione contained in the mixture)

EXAMPLE 2

5 g of 4-androsten-3,17-dione/1,4-androstadien-3,17-dione (4 g/1 g) are suspended in 16 ml methanol, reacted with 1.6 ml water and 5 ml acetoncyanohydrine, and adjusted to a temperature of 40° C. The mixture is then adjusted to a pH of 8.7 through addition of NaOH in methanol, under stirring, and after about 50 minutes the substance mixture is completely dissolved. After a further 15 minutes, the crystallization of 17α-cyano-17α-hydroxy-4-androsten-3-one takes place. Within a further 8 hours, at 40° C., a further 21 ml water is added, and the mixture is then cooled to +15° C. At this temperature it is stirred for a further 3 hours. The crystalline product is sucked off, washed with water in a frit, extensively sucked dry, and then dried under vacuum.

Yield: 4.11 g (94% of theoretical amount, relative to the 4-androsten-3,17-dione present in the mixture)

The working-up of the mother liquor follows as in Example 1. For purification, the product is dissolved in acetone, filtered across Al$_2$O$_3$, and then brought to crystallization from aqueous acetone.

Yield: 865 mg (79% of theoretical amount, relative to the 1,4-androstadien-3,17-dione present in the mixture)

EXAMPLE 3

As described in Example 1, the reaction is performed, but using isopropanol as solvent, and NaCN as base.

Yield: 3.86 g (94% of theoretical amount, relative to the 4-androsten-3,17-dione contained in the mixture)

The obtained mother liquor is dissolved in 20 ml ethanol and 0.5 ml NaOH. It is then heated for 20 minutes to reflux. The mixture is then placed in water, extracted several times with chloroform, and then compressed to dryness. The residue is withdrawn in acetone, filtered across basic Al$_2$O$_3$, and then brought to crystallization from aqueous acetone.

Yield: 945 mg (75% of theoretical amount, relative to the 1,4-androstadiene-3,17-dione present in the mixture)

It will be understood that each of the elements described above, or two or more together, may also find a useful application in other types of separations differing from the types described above.

While the invention has been illustrated and described as embodied in a process for the separation of 4-androsten-3,17-dione and 1,4-androstadien-3,17-dione, it is not intended to be limited to the details shown, since various modifications and structural changes may be made without departing in any way from the spirit of the present invention.

Without further analysis, the foregoing will so full reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Process for the separation of 4-androsten-3,17-dione and 1,4-androstadien-3,17-dione mixtures, comprising reacting said 4-androsten-3,17-dione/1,4-androstadiene-3,17-dione mixture with HCN-yielding cyanide compound, into a mixture of 17β-cyano-17α-hydroxy-4-androsten-3-one and 17β-cyano-17α-hydroxy-1,4-androstadien-3-one, and separating from said product mixture the difficultly soluble 17β-cyano-17α-hydroxy-4-androsten-3-one through crystallization.

2. Process according to claim 1, further comprising re-splitting said 17β-cyano-17α-hydroxy-4-androsten-3-one into 4-androsten-3,17-dione.

3. Process according to claim 2, further comprising re-splitting the 17β-cyano-17α-hydroxy-1,4-androstadien-3-one remaining in said product solution, directly or after extraction with organic solvent into 1,4-androstadien-3,17-dione, and then isolating the same.

4. Process according to claim 1, wherein said HCN-yielding cyanide compound is selected from the group consisting of acetoncyanohydrine and alkali cyanide.

5. Process according to claim 2, wherein said re-splitting is performed by heating in alkaline solutions of alcohol.

6. Process according to claim 3, wherein said re-splitting of 17β-cyano-17α-hydroxy-1,4-androstaden-3-one is performed by heating in alkaline solutions of alcohol.

* * * * *